US 6,668,623 B2

(12) United States Patent
Tani et al.

(10) Patent No.: US 6,668,623 B2
(45) Date of Patent: Dec. 30, 2003

(54) METHOD AND APPARATUS FOR ANALYZING ORGANIC MACROMOLECULAR COMPONENT AND APPLICATION THEREOF

(75) Inventors: Michiko Tani, Omiya (JP); Yutaka Hayashibe, Omiya (JP); Masaaki Kato, Omiya (JP); Minoru Takeya, Omiya (JP)

(73) Assignee: Mitsubishi Materials Corporation, Tokyo (JP)

( * ) Notice: Subject to any disclaimer, the term of this patent is extended or adjusted under 35 U.S.C. 154(b) by 115 days.

(21) Appl. No.: 09/796,468

(22) Filed: Mar. 2, 2001

(65) Prior Publication Data

US 2001/0019843 A1 Sep. 6, 2001

(30) Foreign Application Priority Data

Mar. 3, 2000 (JP) .......................... 2000-059219
Jan. 29, 2001 (JP) .......................... 2001-019767

(51) Int. Cl.$^7$ .................. G01N 30/06; G01N 30/48; G01N 1/18; B01D 15/08
(52) U.S. Cl. ............ 73/61.52; 73/61.53; 73/61.55; 73/61.56; 73/61.58; 210/635; 210/656; 210/198.2; 422/70; 436/86; 436/161; 436/177; 436/178
(58) Field of Search .............. 73/61.52, 61.53, 73/61.55, 61.56, 61.58; 422/68.1, 70, 81; 436/86, 161, 177, 178; 210/198.2, 635, 656

(56) References Cited

U.S. PATENT DOCUMENTS 3,615,224 A * 10/1971 Stern et al. .............. 73/61.52
3,856,471 A * 12/1974 Winitz et al. .............. 422/70
5,843,788 A * 12/1998 Rexroad, Jr. et al. ....... 436/161
6,260,407 B1 * 7/2001 Petro et al. ................ 73/61.52
6,498,040 B1 * 12/2002 Yokoyama et al. ........ 73/61.55

FOREIGN PATENT DOCUMENTS

JP    2000-171451    * 6/2000    ................ 73/61.53
JP    2000-171452    * 6/2000    ................ 73/61.55

OTHER PUBLICATIONS

U.S. patent application Ser. No. 09/820,794, filed Mar. 30, 2001, pending.

* cited by examiner

Primary Examiner—Daniel S. Larkin
(74) Attorney, Agent, or Firm—Oblon, Spivak, McClelland, Maier & Neustadt, P.C.

(57) ABSTRACT

A method and apparatus for efficiently analyzing an organic macromolecular component contained in a sample with high precision are provided. The method and apparatus for analyzing the organic macromolecular component are based on a flow analysis method with a measuring system including a sample introducing section, a preparing section, and a measuring section, composed of steps of supplying a sample with a carrier solution into the measurement system through the introducing section, leading the sample to the preparing section and separating an organic macromolecular component in the sample, and leading the separated organic macromolecular component to the measuring section and analyzing. Herein, the step of separating the organic macromolecular component includes steps of the organic macromolecular component in the sample being adsorbed on a resin and introducing an eluant into the preparing section and eluting the organic macromolecular component adsorbed on the resin.

15 Claims, 4 Drawing Sheets

QUANTITATIVE ANALYSIS OF GELATIN IN COPPER ELECTROLYTIC SOLUTION (POOR DECOMPOSITION)

FIG. 4

QUANTITATIVE ANALYSIS OF GELATIN IN COPPER ELECTROLYTIC SOLUTION (GOOD DECOMPOSITION)

FIG. 5

QUANTITATIVE ANALYSIS OF GELATIN AT ROOM TEMPERATURE

FIG. 6

QUANTITATIVE ANALYSIS OF GELATIN AT ELEVATED TEMPERATURE (75°C)

METHOD AND APPARATUS FOR ANALYZING ORGANIC MACROMOLECULAR COMPONENT AND APPLICATION THEREOF

BACKGROUND OF THE INVENTION

1. Field of the Invention

The present invention relates to a method and an apparatus for analyzing an organic macromolecular component in a solution based on a flow analysis method and to applications thereof. In particular, the present invention relates to an analytical method and an apparatus suitable for quantitatively analyzing very small amounts of glues or gelatins contained in metallic electrolytic solutions, such as copper electrolytic solutions and plating solutions.

2. Description of the Related Art

Various additives are added to electrolytic solutions and plating solutions in accordance with various purposes of improving brightness and smoothness of electrodeposited metal surfaces, hardening plated layers, etc. As the additive, in general, glues are used in electrolytic smelting and gelatins are used in plating. Herein, it is very important in quality control to keep concentrations thereof within specified ranges. For example, although glues are used for improving smoothness of electrodeposited surfaces, when concentrations thereof are too high, polarization is increased to a great degree so that there are problems of deposition of impurities, such as bismuth, contained in the electrolytic solutions, etc.

Therefore, a method for analyzing proteins, such as glues or gelatins, contained in solutions with a high degree of precision has been required. Most of conventional methods for analyzing proteins are performed under from weakly acidic to weakly basic conditions, and there are few analytical methods which can be applied under strongly acidic conditions of pH 1 or less, as in electrolytic solutions, plating solutions, etc. Hitherto, proteins, such as glues or gelatins, contained in electrolytic solutions, plating solutions, etc., have been measured by potentiometric titration, Kjeldahl method, etc., although specific apparatuses and complicated operations have been required in those cases. In the Kjeldahl method, glues are measured after being decomposed into nitrogen in a state of ammonia, although in many cases, nitrogen compounds other than proteins are contained in the electrolytic solutions so as to make precise measurements difficult.

In addition, as a quantitative method for analyzing gelatins and glues in the strongly acidic solution, a method in which those are collected on membrane filters, are bonded with a specific reagent (Amide Black 10B coloring matter), and after excess coloring matters are washed out, the coloring matters are eluted so as to determine gelatins, etc., (Japanese Unexamined Patent Application Publication No. 2-69660), a method in which after gelatins, etc., have been collected on a filter, the resulting filter is dried so as to determine gelatins, etc., based on reflectance (Japanese Unexamined Patent Application Publication No. 6-337247), etc., are reported. Regarding these methods, there are, however, problems that an amount of collected glues is much affected by pore diameters of the filter so as to increase measurement errors, a filtering apparatus for collecting with the filter is required and operations are complicated, and the analytical cost is increased due to disposable filters.

SUMMARY OF THE INVENTION

The present invention has solved the aforementioned problems in conventional analytical methods. It is an object of the present invention to provide a flow analysis method and an apparatus, thereby organic macromolecular components, such as glues and gelatins, in a solution can be promptly and precisely determined even in a strongly acidic solution.

The present invention is due to the completion of a system for measurement with a high degree of reliability and with ease of handling, in which operations of separating organic macromolecular components in a solution by adsorption on a resin, leading these to a gel permeation chromatograph, and analyzing are performed based on the flow analysis.

That is, the present invention relates to the following flow analysis method for separating and analyzing an organic macromolecular component in a sample.

(1) A method for analyzing an organic macromolecular component based on a flow analysis method with a measuring system including a sample introducing section, a preparing section, and a measuring section, composed of steps of supplying a sample with a carrier solution into the measuring system through the introducing section, leading the sample to the preparing section and separating an organic macromolecular component in the sample, and leading the separated organic macromolecular component to the measuring section and analyzing. Herein, the step of separating the organic macromolecular component includes steps of the organic macromolecular component in the sample being adsorbed on a resin and introducing an eluant into the preparing section and eluting the organic macromolecular component adsorbed on the resin.

(2) A method of analysis according to the aforementioned method (1), further composed of the steps of supplying the sample into the measurement system through the introducing section while a pipeline for feeding the sample from the introducing section to the preparing section and a pipeline for discharging a solution from the preparing section out of the measurement system are communicated with the preparing section, leading the sample to the preparing section, the organic macromolecular component in the sample being adsorbed on the resin in the preparing section while leading the solution discharged from the preparing section out of the measurement system, switching pipelines communicating with the preparing section so that a pipeline for supplying the eluant and a pipeline connected to the measuring section communicate with the preparing section, introducing the eluant into the preparing section so as to elute the organic macromolecular component adsorbed on the resin, and leading the resulting solution containing the organic macromolecular component to the measuring section and analyzing.

(3) A method of analysis according to the aforementioned method (1), in which the eluant is used after a buffer solution for preventing the organic macromolecular components from coagulating is added thereto or the buffer solution is added to the solution containing the organic macromolecular component between the preparing section and the measuring section.

(4) A method of analysis according to the aforementioned method (1) or (2), in which gel permeation chromatography is used as an analyzing device so as to fractionate and analyze the organic macromolecular component separated from the sample.

(5) A method of analysis according to the aforementioned method (1) or (2), in which an amount of glues or gelatins separated from the sample or an amount of decomposition products thereof is measured.

(6) A method of analysis according to the aforementioned method (1) or (2), in which gel permeation chromatography is used as an analyzing device so as to fractionate glues or gelatins separated from the sample and to measure the amount thereof or an amount of decomposition products thereof.

(7) A method of analysis according to the aforementioned method (1) or (2), in which an acid-proof and hydrophobic adsorption resin is used as a resin for adsorbing the organic macromolecular component in the sample.

(8) A method of analysis according to the aforementioned method (1) or (2), in which an electrolytic solution taken from a step of metallic electrolysis or a plating solution taken from a step of plating is used as a sample solution.

(9) A method for controlling a step of metallic electrolysis with a method of analysis according to the aforementioned method (1) or (2), in which the method of analysis is further composed of steps of taking a sample solution from an electrolytic solution in the step of metallic electrolysis, measuring an amount of glues or gelatins separated from the sample of the electrolytic solution or an amount of decomposition products thereof, and feeding back the analytical results of the measurement to the step of metallic electrolysis.

(10) A method for controlling a step of plating with a method of analysis according to the aforementioned method (1) or (2), in which the method of analysis is further composed of steps of taking a sample solution from a plating solution in the step of plating, measuring an amount of glues or gelatins separated from the sample of plating solution or an amount of decomposition products thereof, and feeding back the analytical results of the measurement to the step of plating.

In the method of analysis according to the present invention, as described above, a series of operations of separating proteins and organic macromolecular components such as glues and gelatins contained in the solution by adsorption on the resin, leading these to a gel permeation chromatograph, and analyzing are performed based on the flow analysis method. Since operations of the introduction of the sample to the analysis of the organic macromolecular component can be continuously performed in a short time, the analytical results can be promptly obtained. Therefore, regarding the organic macromolecular component, behaviors during decomposition and intermediate products can be grasped. Since separation is performed using the hydrophobic adsorption resin and analysis is performed using the gel permeation chromatography, the organic macromolecular component can be analyzed independent of the molecular weight. Furthermore, when the organic macromolecular components are fed to the measuring section, a buffer solution for preventing the coagulation thereof may be added so as not to cause a blockage of pipeline, etc., and therefore, the analysis can be performed with a high degree of reliability. This buffer solution may be blended beforehand to the eluant or may be added between the preparing section and the measuring section. When the buffer solution is added after the organic macromolecular components adsorbed on the resin are eluted, an effect of eluting is improved and an effect of preventing the organic macromolecular components from coagulating is also improved.

The flow analysis method according to the present invention can be applied to strongly acidic solutions, such as metallic electrolytic solutions and plating solutions, by using an acid-proof and hydrophobic adsorption resin as the resin for adsorbing the organic macromolecular components. Therefore, the quantitative analysis of glues contained in electrolytic solutions of copper electrolytic smelting, etc., can be easily performed so that it can be used as a method for controlling electrolytic operations. According to the method of analysis of the present invention, since a continuous automatic analysis is possible instead of a conventional batch method for controlling electrolysis by the manual work, accurate operation control of the electrolytic smelting for long time is possible.

The present invention further relates to the following apparatuses for flow analysis.

(11) An apparatus for flow analysis of an organic macromolecular component composed of a sample introducing section, a preparing section, and a measuring section integrally connected by pipelines, in which the preparing section is provided with an adsorbing device for the organic macromolecular component and an eluting device for the organic macromolecular component as separating devices for the organic macromolecular component in the sample, and the measuring section is provided with a fractionating and analyzing device for the separated organic macromolecular component.

(12) An apparatus for flow analysis according to the aforementioned apparatus for analysis (11), further provided with a column filled with a resin for adsorbing the organic macromolecular component in the sample, and a pipeline for introduction from the introducing section out of the measurement system and a pipeline for elution from a supply source of the eluant to the measuring section each connected to the column so as to be freely switched to each other, the adsorbing device and the eluting device for the organic macromolecular component being composed thereof.

(13) An apparatus for flow analysis according to the aforementioned apparatus for analysis (11) or (12), further provided with a buffering section for addition of a buffer solution for preventing organic macromolecular components from coagulating between the preparing section and the measuring section.

(14) An apparatus for flow analysis according to the aforementioned apparatus for analysis (11) or (12), further provided with a gel permeation chromatograph in the measuring section as an analytical device for the organic macromolecular component.

(15) An apparatus for flow analysis according to the aforementioned apparatus for analysis (11) or (12), further provided with a thermostatic chamber in the measuring section, and further provided with a gel permeation chromatograph in the thermostatic chamber.

(16) An apparatus for flow analysis according to the aforementioned apparatus for analysis (11) or (12), further provided with a thermostatic chamber in the measuring section, and further provided with a gel permeation chromatograph including a plurality of columns with different mesh diameters of gels in the thermostatic chamber.

(17) An apparatus for flow analysis according to the aforementioned apparatus for analysis (11) or (12), further provided with an automatically controlling device for feed of solution and discharge of solution in the sample introducing section and in the preparing section, temperature adjustment in the measuring section, and actions of a detecting section so as to continuously and automatically perform operations of from sample introduction to fractionation and analysis by way of separation of the organic macromolecular component.

According to the aforementioned apparatus for flow analysis, the organic macromolecular components contained in the sample can be separated with ease of operation and can be analyzed. Furthermore, the column for adsorbing the organic macromolecular components and the pipelines for sample introduction and for leading the separated organic macromolecular component to the measuring section connected to the resin column so as to be freely switched to each other are provided. Therefore, feed of the sample to the resin column and discharge, adsorption and desorption of the organic macromolecular component by the resin, and feed of the solution to the measuring section can be mechanically and smoothly performed in a short time. By the buffering section being provided between the preparing section and the measuring section, separated organic macromolecular components are prevented from coagulating so as not to cause a blockage of the pipeline and the analysis can be performed with a high degree of reliability. By the columns with different mesh diameters of gels for gel permeation chromatography being provided in a plurality of stages in the thermostatic chamber, precise analysis can be performed according to the molecular weight of the organic macromolecular component. In the apparatus for analysis according to the present invention, since the measurement system of from the sample introducing section to the measuring section by way of the preparing section is integrally communicated by pipelines, and pipelines connected to the preparing section are formed so as to be freely switched to each other, operations of feeding solution and discharging solution in each section can be automatically controlled. Therefore, a series of operations of from introduction of the sample to analysis can be automated with the aforementioned automatically controlling device being provided.

DESCRIPTION OF THE PREFERRED EMBODIMENTS

Figure 1:
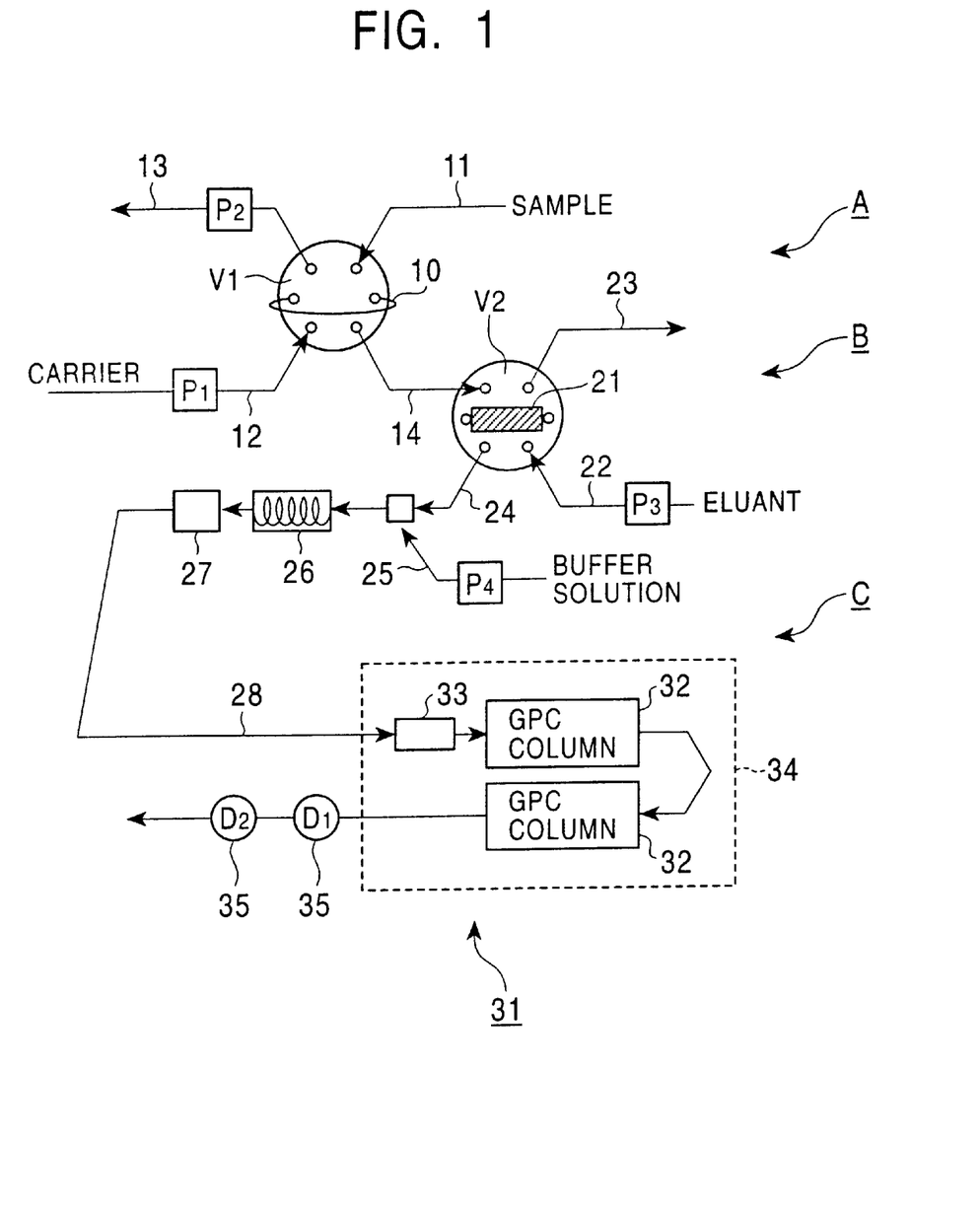
FIG. 1 is a conceptual diagram of an analytical system according to the present invention.
Figure 2:
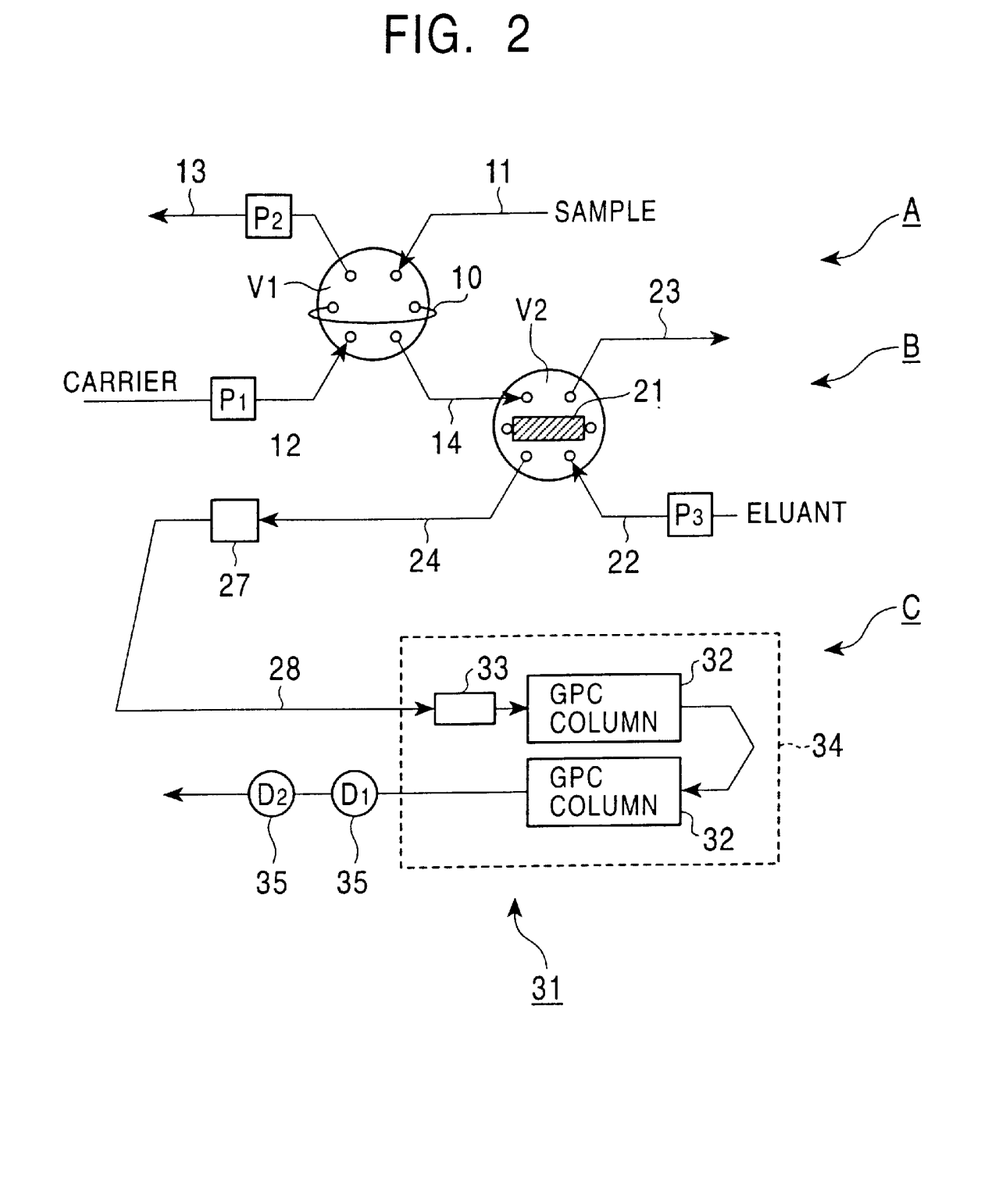
FIG. 2 is a simplified conceptual diagram of an analytical system as shown in FIG. 1.

The present invention will be specifically explained using the following embodiments with reference to the drawings showing a method of analysis and an apparatus according to the present invention. FIGS. 1 and 2 are conceptual diagrams showing examples of the configuration of an analytical system according to the present invention. In the analytical system according to the present invention as shown in the drawings, a sample solution introducing section A, a sample preparing section B, and a measuring section C are sequentially and integrally communicated by pipelines. In the sample preparing section B, a resin-filled column 21 for adsorbing organic macromolecular components in the sample solution and a pipeline 22 for an eluant communicating with the column 21 are provided. In the measuring section C, columns 32 of a gel permeation chromatograph 31 and detecting devices 35 thereof communicating with the column 21 are provided.

In the analytical system as shown in FIG. 1, a pipeline 25 for a buffer solution and a mixing section 26 are further provided between the column 21 in the sample preparing section B and the measuring section C. The columns 32 with different mesh diameters of gels for gel permeation chromatograph 31 are provided in a plurality of stages in a thermostatic chamber 34. The analytical system as shown in FIG. 2 has a simplified configuration in which the pipeline 25 for the buffer solution and the mixing section 26 are omitted from the configuration as shown in FIG. 1.

The sample solution introduced in the measurement system is led to the aforementioned column 21, and the organic macromolecular components in the sample solution are adsorbed and separated. Then, the pipeline is switched so as to feed the eluant into the column and the organic macromolecular components are eluted. Thereafter, the resulting solution containing the organic macromolecular components is led to the columns 32 of the gel permeation chromatograph 31 and the detecting devices 35 thereof so as to be fractionated and analyzed.

Each constituent of the aforementioned analytical system will be explained below.

(A) Sample Introducing Section

The introducing section A for the sample solution includes an introducing device for the sample solution and a feeding device for a carrier solution transferring the sample solution to the measurement system. As the feeding device for the carrier solution, a solution feed pump $P_1$ can be used. As the solution feed pump $P_1$, a plunger pump with less pulsating flow is suitable. Dilute sulfuric acid as the carrier solution is fed to the measurement system through a pipeline 12 by the solution feed pump $P_1$. Dilute sulfuric acid and water may be separately introduced in the system using, for example, a double-plunger pump provided with a solution feed pump for supplying water and a solution feed pump for supplying dilute sulfuric acid as the solution feeding device $P_1$.

As the introducing device for the sample solution, a valve device (six-way valve) $V_1$ provided with a loop 10 for holding a specified amount of sample solution is used. This valve device $V_1$ is provided with six connection holes. The loop 10 for holding a specified amount of sample solution is provided between a pair of the holes on opposite sides, and each of the other connection holes is formed so as to communicate with a pipeline 11 for supplying the sample solution, a pipeline 12 for introducing the carrier solution, a pipeline 13 for discharging the solution, and a pipeline 14 for transferring the solution to the measuring section. In the pipeline 13 for discharging the solution, a solution feed pump $P_2$ is provided.

The sample solution is suctioned by the solution feed pump $P_2$, and is introduced into the aforementioned loop 10 through the pipeline 11 for supplying the sample solution so that a specified amount of the sample solution is held. The amount of the sample solution can be controlled with the length of the loop. During the measurement, the loop 10 is communicated with the pipeline 12 for introducing the carrier solution and the pipeline 14 for the measurement system, respectively, according to the turn of the valve device $V_1$ so that a specified amount of the sample solution is fed to the sample preparing section B by the carrier solution. After the sample solution is fed, the pipelines are switched by the turn of the valve device $V_1$ and the loop 10 is communicated with the pipeline 11 for supplying the sample solution and the pipeline 13 for discharging the solution so that a remaining solution in the loop is discharged and new sample solution is introduced into the loop 10. A plurality of sample solution tanks, although not shown in the drawings, may be connected to the pipeline 11 for supplying the sample solution with a switching device for pipelines, although not shown in the drawings, therebetween so as to appropriately select the sample solution to be introduced in the measurement system from a plurality of sample solutions.

(B) Sample Preparing Section

The sample preparing section B is provided with the resin-filled column 21 and the pipeline 22 for the eluant communicating with the column 21. In the analytical system as shown in the drawings, a valve device $V_2$ having six connection holes is provided similarly to the valve device $V_1$ in the sample introducing section, and the aforementioned column 21 is provided between a pair of the holes on opposite sides of the valve device $V_2$. Each of the other connection holes is formed so as to communicate with a pipeline 14 for connecting to the introducing section A, the pipeline 22 for the eluant, a pipeline 23 for discharging the solution, and a pipeline 24 for the measurement system transferring to the measuring section C.

The aforementioned column 21 is filled with the resin for adsorbing organic macromolecular components contained in the sample solution. Specifically, for example, when the sample solution is a metallic electrolytic solution or a plating solution, a hydrophobic adsorbing resin adsorbing proteins, such as glues and gelatins, contained in the solution is applied as the filler. As this resin, an acid-proof hydrophobic adsorbing resin is suitable so as to tolerate strongly acidic solutions, such as the metallic electrolytic solution and the plating solution. Styrene-divinylbenzene-based nonpolar resins, ester-based resins of intermediate polarity, etc., are used as preferable resins. The nonpolar resins and resins of intermediate polarity have superior performance of adsorbing very small amounts of proteins in the solution compared to ion exchange resins. The styrene-divinylbenzene-based resins have high durability against acids.

A solution feed pump $P_3$ is provided in the pipeline 22 for the eluant. After the channel of the aforementioned column 21 is switched according to the turn of the valve device $V_2$ so as to communicate with the pipeline 22 for the eluant and the pipeline 24 for the measurement system, the eluant is introduced in the column 21. As the eluant, aqueous solutions of organic solvents can be used. Specifically, aqueous solutions of lower alcohols such as methanol and ethanol, acetonitrile, etc., can be used. Among these, acetonitrile has a superior effect of eluting. The concentration of the eluant is preferably 20 to 50% by weight. When the concentration is too low, elution of proteins is insufficient. On the other hand, when the concentration is too high, proteins precipitate so as to hinder the feed of the solution and the measurement.

A specified amount of the sample solution is introduced in the column 21 from the introducing section A through the pipeline 14. The organic macromolecular components in the solution are adsorbed on the resin, and the filtrate passed through the column is discharged out of the system through the pipeline 23. After completion of the adsorption, pipelines are switched according to the turn of the valve device $V_2$ so that the column 21 is communicated with the pipeline 22 for the eluant and pipeline 24 for the measurement system. Then the eluant is introduced into the column. The organic macromolecular components adsorbed on the resin are eluted into the solution by the eluant, and is fed to the measuring section C through the pipeline 24. Regarding low concentration of proteins, etc., the concentration of the proteins can be increased with repeating the adsorption by the resin.

Before the introduction of the sample solution and the eluant into the resin-filled column 21, if necessary, conditioning of the inside of the column is preferably performed. For example, dilute sulfuric acid solution is passed beforehand through the column and the inside of the column is preferably replaced by the carrier solution so as to prevent metals from depositing and to promote the adsorption of the proteins. When the concentration of acids in the column is high, washing with water is preferably performed beforehand.

In the analytical system as shown in FIG. 1, the pipeline 25 for the buffer solution, a solution feed pump $P_4$ therefor, and the mixing section 26 are provided between the sample preparing section B and the measuring section C. The buffer solution prevents eluted proteins (organic macromolecular components), such as glues and gelatins, from coagulating. Neutral or weakly acidic solutions, such as phosphoric acid, are used as the buffer solution. The buffer solution is introduced in the pipeline 24 for the measurement system by the solution feed pump $P_4$, then is added to the eluant containing the organic macromolecular components, and is uniformly mixed during passing through the mixing section 26. The mixing section 26 is formed of the coiled part of the pipeline 24 so as to increase the length of the pipeline, and thereby, the mixing time is ensured. A degasser 27 is provided at the outlet of the mixing section 26 for degassing. The eluant containing the organic macromolecular components mixed with the buffer solution is introduced in the measuring section C through a pipeline 28 for the measurement system after passing through the mixing section 26.

As shown in FIG. 2, by using the buffer solution mixed beforehand with the eluant, the pipeline 25 for introducing the buffer solution and the mixing section 26 may be omitted so as to simplify the measurement system. When the effect of eluting is decreased, the pipeline 25 for introducing the buffer solution may be provided as shown in FIG. 1 so that the eluant and the buffer solution are preferably separately introduced.

(C) Measuring Section

The measuring section C is provided with the gel permeation chromatograph (GPC) 31 as a measuring device. The gel permeation chromatograph 31 includes the GPC columns 32 and the detecting devices 35. Regarding the GPC columns 32, a plurality of columns filled with different mesh diameters of gels are provided in a plurality of stages so as to fractionate and analyze proteins, that is, organic macromolecular components, having wide distribution of molecular weights. In order to suppress the error due to the change in temperature, these gel-filled columns are provided in the thermostatic chamber 34. In order to protect the GPC columns 32, a guard column 33 is provided before the GPC columns 32.

The organic macromolecular components, such as proteins introduced into the GPC columns 32 are diffused along the direction of flow according to the mesh diameters of the gels in response to the molecular weights during passing through the columns. Specifically, for example, proteins having a molecular weight of 10,000 or less are fractionated and diffused in the first stage column 32, and proteins having a molecular weight of 10,000 or more are fractionated and diffused in the second stage column 32. The resulting solution in which proteins, etc., are diffused is led to the detecting devices 35 so as to be quantitated.

As the detecting device 35, a method of direct and optical quantitation of proteins, etc., can be used. The measuring section C may be provided with a pipeline for introducing a coloring agent and a mixing section so as to quantitate based on the strength of coloring, etc.

The analytical system according to the present invention preferably includes an automatically controlling device.

That is, the automatically controlling device in which operations of each solution feed pump and valve device provided in the sample solution introducing section, temperature adjustment of the measuring section, and actions of the detecting section are controlled and a series of operations of from introducing the sample solution to fractionating and analyzing the organic macromolecular components, such as proteins, are continuously and automatically performed may be provided. According to the aforementioned automatic analytical system, glues in the electrolytic solution, etc., can be grasped in real time.

(a) According to the flow analysis system (method or apparatus) of the present invention, the quantitative analysis of proteins, etc., which has been hitherto individually and manually performed, can be mechanically and promptly performed in a short time with no measurement error due to the manual work and with high measurement precision. Furthermore, the analytical time can be decreased to a great degree. In particular, since proteins, etc., can be fractionated and analyzed according to the molecular weight, behaviors during decomposition and the amount of intermediate products, etc., of glues, etc., contained in the sample solution can be grasped. In addition, since proteins can be analyzed after being concentrated by repeating the adsorption on the resin, low concentration of proteins, etc., can be fractionated and analyzed. As described above, the analytical system according to the present invention can be used as a method for process control of electrolytic operations.

(b) The apparatus for analysis according to the present invention is suitable for automation since the analysis is based on the flow analysis in which separation of protein, etc., addition of agents, reaction, and analysis are continuously performed during the sample solution flows through pipelines. By automation, the analytical time can be further decreased and factors of errors can be also further decreased so that the measurement precision can be improved.

(C) In particular, the apparatus for analysis according to the present invention is suitable for the quantitation of very small amounts of proteins, etc., contained in strongly acidic solutions, such as electrolytic solutions and plating solutions. Since proteins dissolved in strongly acidic solutions are likely to be decomposed and be denatured, when the analytical time is long, the measurement precision is decreased to a great degree. Conventional batch type analytical methods require about twenty-four hours of analytical time and the analytical error is large so that the process control cannot be performed in real time. On the other hand, according to the analytical system of the present invention, the analytical results can be promptly obtained in a very short time after sampling so that the analytical precision is high.

(d) In the analytical system of the present invention, since a hydrophobic adsorption resin is used as a device for separating proteins and conventional filters, etc., are not used, the analytical precision does not depend on pores of filters. The aforementioned adsorption resin can be easily regenerated and can be repeatedly used so that the analytical cost can be decreased.

EXAMPLES

The present invention will be specifically explained below using the examples.

Example 1

A quantitative analysis of gelatins in a copper electrolytic solution containing 1.5 M of sulfuric acid, 40 g/L of copper, and 20 g/L of nickel was performed using the analytical system according to the present invention as shown in FIG. 1. A resin-filled column 21 for adsorbing proteins is formed of a tube of 1 mm in diameter, 150 mm in length and 0.11 mL in volume filled with a hydrophobic nonpolar adsorbing resin SM-2 (trade name). 1 mL of sample solution was used. Dilute sulfuric acid in concentration of 0.1 M was used as a carrier solution, and 40% acetonitrile aqueous solution was used as an eluant of proteins. The first stage GPC column 32 was filled with a hydrophilic polymer gel with an exclusion molecular weight limit of $2.0 \times 10^5$, and the second stage GPC column 32 was filled with the hydrophilic polymer gel with an exclusion molecular weight limit of $2.5 \times 10^6$. As detecting devices 35, ultraviolet and visible spectrophotometers equipped with a flow cell having an optical path length of 20 mm were used at a measurement wave length of 209 nm.

After dilute sulfuric acid and water were passed through the resin-filled column 21 for washing, the sample solution was passed through the sample loop 10 so as to be held by a specified amount of 1 mL. Then dilute sulfuric acid as a carrier was introduced into the loop 10 so that the sample solution was fed to the aforementioned column 21 and gelatins in the sample solution were adsorbed on the resin. The solution passed through the column 21 was discharged out of the system. Next, the pipelines were switched so that the eluant was fed into the column 21, the gelatins adsorbed on the resin were eluted, and the resulting eluate was led to the mixing section 26 through the pipeline 24. Phosphoric acid in concentration of 0.1 M was used as a buffer solution, and was mixed with the eluate passing through the pipeline 24. The mixed solution was led to the two stages of GPC columns 32 so as to fractionate and diffuse the gelatins in the solution. The resulting mixed solution was led to the detecting devices 35 and behaviors of the gelatins during decomposition in copper electrolytic solution were measured. The results thereof are shown in FIG. 3 and FIG. 4.

Figure 3:
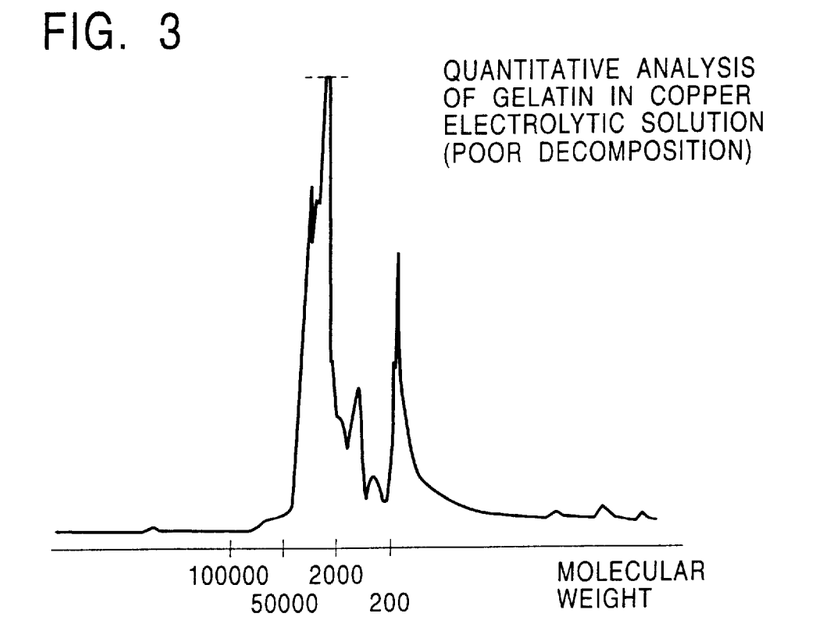
FIG. 3 is a graph showing analytical results according to Example 1.
Figure 4:
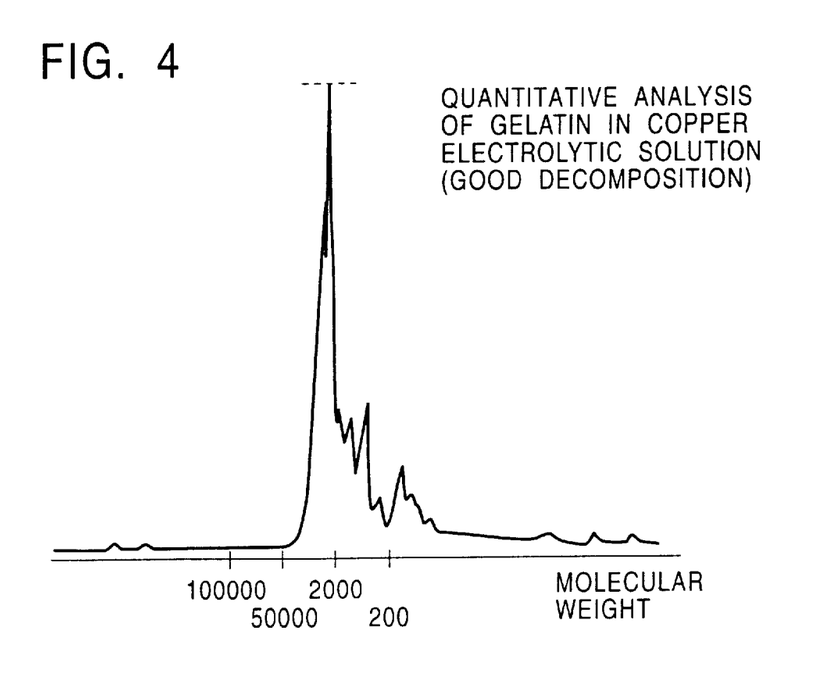
FIG. 4 is a graph showing analytical results according to Example 1.

As shown in FIG. 3, the gradual rise of the chromatogram curve at the molecular weight of about 100,000 to 50,000 in terms of polyethylene oxide indicates poor decomposition of gelatins. In addition, the presence of peaks at the molecular weight in the neighborhood of 200 indicates that intermediate products in this range are generated. On the other hand, as shown in FIG. 4, the sharp rise of the chromatogram curve at the molecular weight of about 50,000 to 2,000 and the presence of no large peak at the molecular weight in the neighborhood of 200 indicate good decomposition of gelatins.

Example 2

Figure 5:
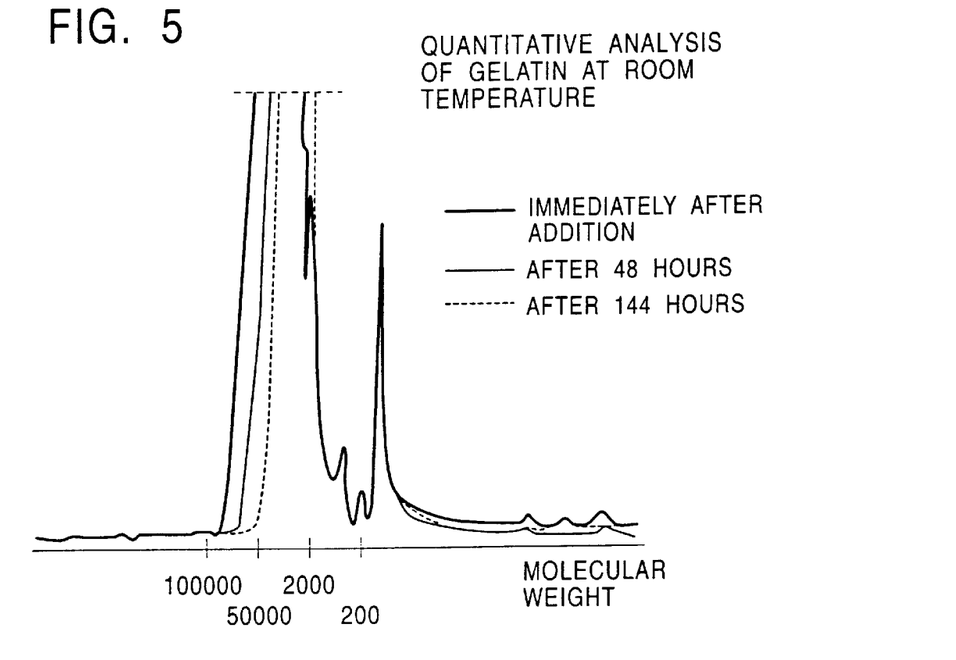
FIG. 5 is a graph showing analytical results according to Example 2.
Figure 6:
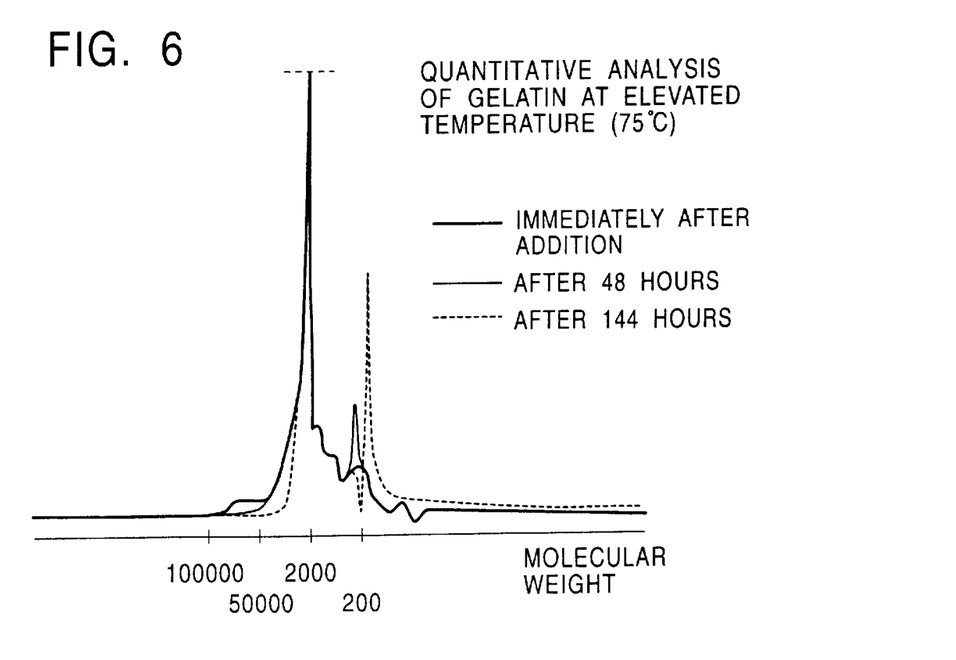
FIG. 6 is a graph showing analytical results according to Example 2.

Regarding the copper electrolytic solution similar to that in the Example 1, behaviors of the gelatins during decomposition in different environments, that is, at room temperature and at an elevated temperature of 75° C., were measured in a manner similar to that in the Example 1. The measurements were continuously performed from immediately after the addition until 144 hours after the addition and changes thereof with time were examined. The results thereof were shown in FIG. 5 and FIG. 6. As shown in the drawings, the chromatogram curve gradually shifts to the low molecular weight side with the passage of measuring time. This indicates that the decomposition of gelatins proceeds with the passage of measuring time. As shown in FIG. 5, the decomposition speed of the gelatins at room temperature is slower than that of the gelatins at the elevated temperature, although the decomposition state of the gelatins after a lapse of twenty-four hours or more is very different from that of the gelatins immediately after the addition. On the other hand, as shown in FIG. 6, at the elevated temperature, the chromatogram curve shifts to a great degree to the low molecular weight side even after a lapse of three hours from the addition. Therefore, it is clear that the prompt analysis in a short time is necessary for controlling the electrolytic solution.

What is claimed is:

1. A method for analyzing at least one organic macromolecular component selected from the group consisting of glue(s) and gelatin(s) with a measurement system, a sample introducing section, a preparing section, and a gel permeation chromatography measuring section, comprising:
supplying a sample with a carrier solution into said measurement system through said introducing section;
leading said sample to said preparing section and separating an organic macromolecular component in said sample; and
leading said separated organic macromolecular component to said gel permeation chromatography measuring section and analyzing,
wherein separating said organic macromolecular component comprises:
adsorbing said organic macromolecular component in said sample on a resin; and
introducing an eluant into said preparing section and eluting said organic macromolecular component adsorbed on said resin.

2. The method according to claim 1, further comprising:
supplying said sample into said measurement system through said introducing section while a pipeline for feeding said sample from said introducing section to said preparing section and a pipeline for discharging a solution from said preparing section out of said measurement system communicate with said preparing section;
leading said sample to said preparing section, and adsorbing said organic macromolecular component in said sample on said resin in said preparing section while leading said solution discharged from said preparing section out of said measurement system;
switching pipelines communicating with said preparing section so that a pipeline for supplying said eluant and a pipeline connected to said measuring section communicate with said preparing section;
introducing said eluant into said preparing section so as to elute said organic macromolecular component adsorbed on said resin; and
leading the resulting solution containing said organic macromolecular component to said gel permeation chromatography measuring section and analyzing.

3. The method according to claim 1, wherein said eluant is used after a buffer solution for preventing said organic macromolecular components from coagulating is added thereto or said buffer solution is added to said solution containing said organic macromolecular component between said preparing section and said measuring section.

4. The method according to claim 1, wherein an acid-proof and hydrophobic adsorption resin is used for adsorbing said organic macromolecular component in said sample.

5. The method according to claim 1, wherein an electrolytic solution taken from a step of metallic electrolysis or a plating solution taken from a step of plating is used as a sample solution.

6. The method for controlling a metallic electrolysis process by analyzing the organic macromolecular component according to claim 1, wherein said analyzing the organic macromolecular component further comprises:
taking a sample solution from an electrolytic solution used in said metallic electrolysis;
measuring an amount of glue(s) and gelatin(s) separated from said sample of electrolytic solution; and
feeding back the analytical results of said measurement to control said metallic electrolysis process.

7. The method for controlling a plating process by analyzing the organic macromolecular component according to claim 1, wherein said analyzing the organic macromolecular component further comprises:
taking a sample solution from a plating solution in said plating;
measuring an amount of glue(s) and gelatin(s) separated from said sample of plating solution; and
feeding back the analytical results of said measurement to control said plating process.

8. The method according to claim 1, wherein said eluant is acetonitrile.

9. An apparatus for flow analysis of at least one organic macromolecular component selected from the group consisting of glue(s) and gelatin(s) comprising a sample introducing section, a preparing section, and a measuring section integrally connected by pipelines, wherein said preparing section comprises an adsorbing device for said organic macromolecular component and an eluting device for said organic macromolecular component as separating devices for said organic macromolecular component in a sample, and said measuring section comprises a gel permeation chromatograph for fractionating and analyzing the separated organic macromolecular component.

10. The apparatus according to claim 9, further comprising:
a column filled with a resin for adsorbing said organic macromolecular component in said sample; and
a pipeline for introduction from said introducing section out of said measurement system and a pipeline from a supply source of said eluant to said measuring section, each connected to said column so as to be freely switched to each other, said adsorbing column and an eluting device for said organic macromolecular component communicating by pipelines.

11. The apparatus according to claim 9, further comprising a buffering section for addition of a buffer solution for preventing organic macromolecular components from coagulating between said preparing section and said measuring section.

12. The apparatus according to claim 9, further comprising a thermostatic chamber in said measuring section, and further comprising a gel permeation chromatograph in said thermostatic chamber.

13. The apparatus according to claim 9, further comprising a thermostatic chamber in said measuring section, and further comprising a gel permeation chromatograph comprising a plurality of columns with different mesh diameters of gels in said thermostatic chamber.

14. The apparatus according to claim 9, further comprising an automatic controlling device for feed of solution and discharge of solution in said sample introducing section and in said preparing section, a temperature adjustment device in said gel permeation chromatography measuring section, and a detecting section to perform continuous and automatic operations of from sample introduction to fractionation and analysis by separation of said organic macromolecular component.

15. The apparatus according to claim 9, wherein said eluting device comprises acetonitrile.

* * * * *